United States Patent
Xu et al.

(10) Patent No.: US 11,961,594 B2
(45) Date of Patent: Apr. 16, 2024

(54) SYSTEM AND METHOD USING CLINICAL DATA TO PREDICT GENETIC RELATEDNESS FOR THE EFFICIENT MANAGEMENT AND REDUCTION OF HEALTHCARE-ASSOCIATED INFECTIONS

(71) Applicant: KONINKLIJKE PHILIPS N.V., Eindhoven (NL)

(72) Inventors: Liyi Xu, Cambridge, MA (US); Raivo Kolde, Melrose, MA (US); Andrew G. Hoss, Cambridge, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1243 days.

(21) Appl. No.: 16/455,985

(22) Filed: Jun. 28, 2019

(65) Prior Publication Data
US 2020/0411133 A1    Dec. 31, 2020

(51) Int. Cl.
*G16B 5/20*    (2019.01)
*G06N 5/02*    (2023.01)
(Continued)

(52) U.S. Cl.
CPC ............ *G16B 5/20* (2019.02); *G06N 5/02* (2013.01); *G16B 20/20* (2019.02); *G16B 30/10* (2019.02);
(Continued)

(58) Field of Classification Search
CPC ......... G16B 5/20; G16B 20/20; G16B 30/10; G16B 45/00; G16B 20/40; G16B 40/20;
(Continued)

(56) References Cited

U.S. PATENT DOCUMENTS 10,685,740 B2 *  6/2020  Kamalakaran ......... G16B 45/00
10,902,936 B2 *  1/2021  Lin ........................ G16B 20/50
(Continued)

FOREIGN PATENT DOCUMENTS

CN    109871866 A    6/2019
WO    2017072707 A1  5/2017

OTHER PUBLICATIONS

Duclos-Gosselin, Louis, Benny Rigaux-Bricmont, and René Yves Darmon. "How Health Managers Can Use Data Mining for Predicting Individuals' Risks of Contracting Nosocomial Pneumonia." Health Marketing Quarterly 32.1 (2015): 1-13. (Year: 2015).*
(Continued)

*Primary Examiner* — Jesse P Frumkin

(57) ABSTRACT

A method for identifying two or more infections as related or non-related infections based on an estimated genetic relatedness of the two or more infections, comprising: (i) receiving, for each of two or more infected patients, infection-relevant information comprising an antibiotic resistance profile for the patient's infection, a geo-temporal record for the patient, and a caregiver history for the patient; (ii) estimating, using a trained genetic relatedness model, a genetic relatedness of at least two of the two or more infections; (iii) comparing the estimated genetic relatedness between at least two of the two or more infections to a predetermined threshold; (iv) identifying, based on the comparison, the at least two of the two or more infections as a related infection or a non-related infection.

14 Claims, 5 Drawing Sheets

300

Patients with microbial infections

Co-location metrics

Timeline of patients' stay

Temporal distances

Timeline of MIC testing

MIC profiles

Resistance
Inhibitory
Sensitive
NA

(51) Int. Cl.
*G16B 20/20* (2019.01)
*G16B 30/10* (2019.01)
*G16B 40/20* (2019.01)
*G16B 45/00* (2019.01)
*G16H 40/20* (2018.01)
*G16H 50/30* (2018.01)
*G16H 50/50* (2018.01)
*G16H 50/70* (2018.01)
*G16H 50/80* (2018.01)
*G16H 70/60* (2018.01)
*G16B 20/40* (2019.01)

(52) U.S. Cl.
CPC .............. *G16B 45/00* (2019.02); *G16H 40/20* (2018.01); *G16H 50/30* (2018.01); *G16H 50/50* (2018.01); *G16H 50/70* (2018.01); *G16H 50/80* (2018.01); *G16H 70/60* (2018.01); *G16B 20/40* (2019.02); *G16B 40/20* (2019.02)

(58) Field of Classification Search
CPC .......... G06N 5/02; G16H 40/20; G16H 50/30; G16H 50/50; G16H 50/70; G16H 50/80; G16H 70/60
See application file for complete search history.

(56) References Cited

U.S. PATENT DOCUMENTS

| | | | |
|---|---|---|---|
| 2002/0120408 A1* | 8/2002 | Kreiswirth | G16B 30/10 435/6.15 |
| 2012/0179491 A1* | 7/2012 | Liu | G16H 15/00 705/2 |
| 2015/0234981 A1 | 8/2015 | Naidich | |
| 2018/0052954 A1 | 2/2018 | Kamalakaran et al. | |
| 2019/0087535 A1* | 3/2019 | Lin | G16B 10/00 |
| 2019/0226004 A1* | 7/2019 | Loftus | C12Q 1/025 |

OTHER PUBLICATIONS

Miller, James K. et al., "Statistical outbreak detection by joining medical records and pathogen similarity", Journal of Biomedical Informatics, vol. 91, (Feb. 13, 2019).

Gomez-Vallejo H.J. et al., "A case-based reasoning system for aiding detection and classification of nosocomial infections", Decision Support Systems, Elsevier Science Publishers, NL, vol. 84, (Feb. 20, 2016), pp. 104-116.

International Search Report for PCT/EP2020/067655 dated Jun. 24, 2020.

Pak, et al., "How Next-Generation Sequencing and Multiscale Data Analysis Will Transform Infectious Disease Management", Viewpoints, CID, 2015:61, pp. 1695-1702.

Nguyen, et al., "Using machine learning to predict antimicrobial minimum inhibitory concentrations and associated genomic features for nontyphoidal *Salmonella*", JCM Accepted Manuscript Posted Online, Oct. 17, 2018 J. Clin. Microbiol. doi:10.1128/JCM.01260-18, 30 pages.

Ruesen, et al., "Linking minimum inhibitory concentrations to whole genome sequence-predicted drug resistance in *Mycobacterium tuberculosis* strains from Romania", Scientific Reports 2018, Published online Jun. 26, 2018, pp. 1-8.

* cited by examiner

100

```
┌─────────────────────────────────────────────────────────────────┐
│  Receive infection-relevant information and pathogen sequencing │
│  data for a plurality of patients and their respective infection│
│                              110                                │
└─────────────────────────────────────────────────────────────────┘
                              ▽
┌─────────────────────────────────────────────────────────────────┐
│  Calculate genetic relatedness between the infections of two or │
│  more of the plurality of patients using the received pathogen  │
│  sequencing data                                                │
│                              120                                │
└─────────────────────────────────────────────────────────────────┘
                              ▽
┌─────────────────────────────────────────────────────────────────┐
│  Generate, using the received infection-relevant information and│
│  calculated genetic distances, a predictive model designed to   │
│  provide an estimate of genetic relatedness between two or more │
│  infections using only infection-relevant information           │
│                              130                                │
└─────────────────────────────────────────────────────────────────┘
```

Receive infection-relevant information for two or more infected patients
210

Estimate genetic relatedness of the pathogens using the trained genetic relatedness model
220

Compare the genetic relatedness estimate to one or more thresholds
230

Identify the infections as being related or non-related based on the comparison to the one or more thresholds
240

Provide the estimated genetic relatedness output and/or the identity of the relatedness or non-relatedness of the infections to a user
250

Obtain sequencing data for infections identified by the model as being related
260

Determine, using the sequencing data, the relatedness of the infections
270

FIG. 2

| Patient Pairs | | Co-Located Days | | | Temporal Distance | MIC Distances | | | Caregiver Sharing | |
|---|---|---|---|---|---|---|---|---|---|---|
| | | EICU | 7 East | 7 West | MIC Testing | Anti-1 | Anti-2 | Anti-3 | N. 1 | N. 2 |
| Patient 1 | Patient 2 | 1 | 0 | 4 | 0 | 0 | 4 | 7 | 1 | 0 |
| Patient 1 | Patient 3 | 5 | 3 | 0 | 3 | 0 | 8 | 0 | 10 | 0 |
| Patient 2 | Patient 3 | 2 | 2 | 1 | 4 | 2 | 0 | 0 | 5 | 10 |

SYSTEM AND METHOD USING CLINICAL DATA TO PREDICT GENETIC RELATEDNESS FOR THE EFFICIENT MANAGEMENT AND REDUCTION OF HEALTHCARE-ASSOCIATED INFECTIONS

FIELD OF THE DISCLOSURE

The present disclosure is directed generally to methods and systems for estimating the genetic relatedness of two or more infections without sequencing data.

BACKGROUND

Healthcare-associated infections (HAIs) are a growing problem within healthcare settings, with many patients acquiring infections during their healthcare treatments. HAIs can be deadly, and the CDC suggests that 1 out of every 20 hospitalized patients will contact an HAI, resulting in approximately 99,000 death each year in the US hospitals.

Accordingly, identifying an HAI at an early stage is important to pinpoint root causes or sources and to prevent the spread of the invention. Under CDC guidelines, infectious control (IC) staff are required to start investigation every time there are least two cases of the same resistant bug in the same unit in a two-week period. Ideally, IC staff would be able to monitor patients' condition in real-time and identify affected individuals and/or hospital environments that might be infected for sequencing confirmation.

One way to identify an HAI is through determination of the genetic distance (aka relatedness) between patients' infections—or between patients and an environment, or between environments—is with whole genome sequencing. However, the majority of hospitals don't have the capability to sequence patients' samples for infectious disease control purposes. For a small subset of hospital capable of utilizing sequencing, the current method of screening every patient by sequencing is labor and cost-intensive, especially when only 5-10% patients have an HAI. Indeed, the preparation and sequencing cost for a 20× run using Illumina technology is currently approximately $200 per sample. Therefore, sequencing every potential HAI when only 5-10% patients have an HAI would be a waste of money and resources.

SUMMARY OF THE DISCLOSURE

There is a continued need for cost- and resource-effective methods to identify and characterize healthcare-associated infections.

The present disclosure is directed to inventive methods and systems for estimating the genetic relatedness of two or more infections without sequencing data. Various embodiments and implementations herein are directed to a system that receives infection-relevant information for each of two or more infected patients, comprising an antibiotic resistance profile for the patient's infection, a geo-temporal record for the patient, and a caregiver history for the patient. The system uses a trained genetic relatedness model to analyze the received infection-relevant information for the infected patients and to estimate based on that analysis a genetic relatedness of their infections. The system compares the estimated genetic relatedness to a predetermined threshold, and identifies the infections as being related or non-related infections. The system displays, via a user interface, a representation of the estimated genetic relatedness between the at least two of the two or more infections. A healthcare professional such as an infection control agent utilizes the estimated genetic relatedness and relatedness determination, as provided by via the user interface, to make healthcare decisions such as enacting an infection control protocol.

Generally, in one aspect, a method for identifying two or more infections as related or non-related infections based on an estimated genetic relatedness of the two or more infections is provided. The method includes: (i) receiving, for each of two or more infected patients, infection-relevant information comprising an antibiotic resistance profile for the patient's infection, a geo-temporal record for the patient, and a caregiver history for the patient; (ii) estimating, using a trained genetic relatedness model analyzing the received infection-relevant information for the two or more infected patients, a genetic relatedness of at least two of the two or more infections; (iii) comparing the estimated genetic relatedness between at least two of the two or more infections to a predetermined threshold; and (iv) identifying, based on the comparison, the at least two of the two or more infections as a related infection or a non-related infection, wherein the at least two of the two or more infections are identified as a related infection if the estimated genetic relatedness falls below the predetermined threshold, and wherein the at least two of the two or more infections are identified as a non-related infection if the estimated genetic relatedness exceeds the predetermined threshold.

According to an embodiment, the trained genetic relatedness model estimates genetic relatedness of the at least two of the two or more infections without sequencing data.

According to an embodiment, the genetic relatedness of the two or more infections comprises a predicted number of SNPs between at least two of the two or more infections.

According to an embodiment, the method further includes: (i) obtaining, if the at least two of the two or more infections are identified as related, sequencing data for each of the at least two of the two or more infections; and (ii) determining, using the obtained sequencing data, the relatedness of the at least two of the two or more infections.

According to an embodiment, the method further includes displaying, on an interactive user interface, a representation of the estimated genetic relatedness between the at least two of the two or more infections.

According to an embodiment, the representation of the estimated genetic relatedness comprises a network graph of two or more patients and/or infections.

According to an embodiment, the method further includes adjusting, using an interactive user interface, the predetermined threshold.

According to an embodiment, the predetermined threshold is based at least in part on the identity of a pathogen causing the two or more infections.

According to an embodiment, the method further includes training the trained genetic relatedness model, comprising: (i) receiving, from a database of infection data, infection-relevant information for a plurality of patients and pathogen sequencing data for an infection associated with each of the plurality of patients; (ii) calculating, using the sequencing data, genetic relatedness between the infections of two or more of the plurality of patients; (iii) generating, from the received infection-relevant information and the calculated genetic relatedness between the infections, a predictive model designed to provide an estimate of genetic relatedness between two or more infections using only infection-relevant information.

According to an embodiment, the genetic relatedness model comprises a decision tree.

According to an aspect is a system configured to identify two or more infections as related or non-related infections based on an estimated genetic relatedness of the two or more infections. The system includes: infection-relevant information for each of two or more infected patients, comprising an antibiotic resistance profile for the patient's infection, a geo-temporal record for the patient, and a caregiver history for the patient; a trained genetic relatedness model configured to analyze the received infection-relevant information for the two or more infected patients and to estimate based on that analysis a genetic relatedness of at least two of the two or more infections; and a processor configured to: (i) compare the estimated genetic relatedness between at least two of the two or more infections to a predetermined threshold; and (i) identify, based on the comparison, the at least two of the two or more infections as a related infection or a non-related infection, wherein the at least two of the two or more infections are identified as a related infection if the estimated genetic relatedness falls below the predetermined threshold, and wherein the at least two of the two or more infections are identified as a non-related infection if the estimated genetic relatedness exceeds the predetermined threshold; and a user interface configured to display a representation of the estimated genetic relatedness between the at least two of the two or more infections.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

FIG. 1 is a flowchart of a method for training a genetic relatedness model, in accordance with an embodiment.

FIG. 2 is a flowchart of a method for characterizing two or more infections as related or non-related, in accordance with an embodiment.

DETAILED DESCRIPTION OF EMBODIMENTS

The present disclosure describes various embodiments of a system and method for characterizing infections by estimating the genetic relatedness of the infections using a trained model without sequencing data. The system uses a trained genetic relatedness model to analyze infection-relevant information for each of two or more infected patients. The infection-relevant information includes, for example, an antibiotic resistance profile for the patient's infection, a geo-temporal record for the patient, and a caregiver history for the patient. The trained genetic relatedness model estimates, based on the analysis, a genetic relatedness of the patients' infections. Using predetermined thresholds and the estimated genetic relatedness, the system characterizes the patients' infections as related or non-related. A representation of the estimated genetic relatedness between the at least two of the two or more infections is provided to a user such as an infection control agent, who utilizes the information for downstream healthcare decisions.

Referring to FIG. 1, in one embodiment, is a flowchart of a method 100 for training a genetic relatedness model to characterize two or more infections as related or non-related without sequencing data. The method may be performed using any system configured for model generation, including but not limited to the systems described or otherwise envisioned herein.

As an initial step, a trained genetic relatedness model is created to perform the subsequent estimation of genetic relatedness of two or more infections. Accordingly, at step 110 of the method, a system receives infection-relevant information and pathogen sequencing data for a plurality of patients and their respective infection. The system can receive, or request or active obtain, this information from a local or remote database. For example, there may be proprietary or public databases of patient data, anonymized or non-anonymized, that collects this type of data for epidemiological studies or other analysis. Accordingly, an individual or the system may access this data. The system may access the data for analysis, may retrieve or copy the data and store it locally for analysis, or may otherwise use the data accordingly.

Figures 3, 4:
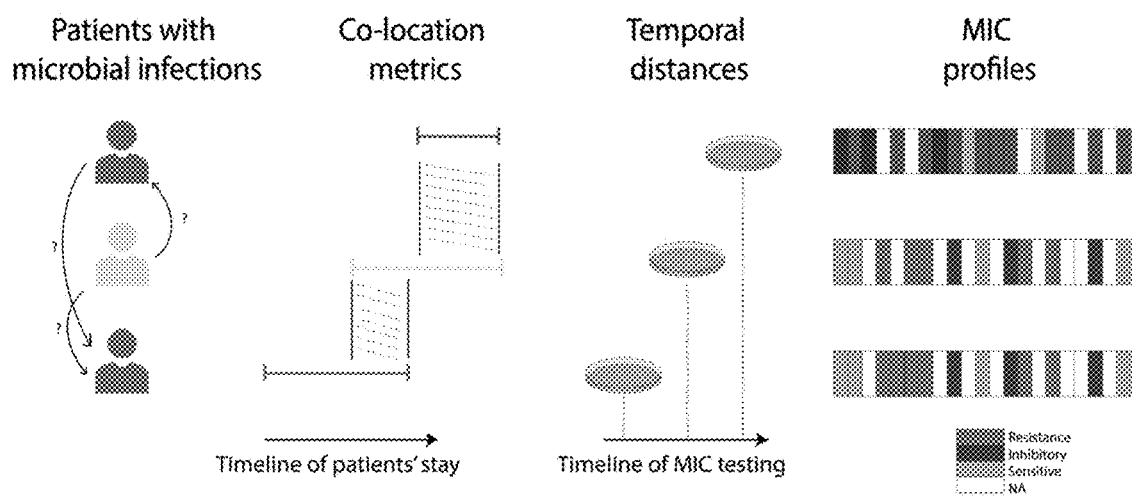
FIG. 3 is a schematic representation of possible categories of infection-relevant information, in accordance with an embodiment.
FIG. 4 is a matrix comprising input information for a genetic relatedness model, in accordance with an embodiment.

Infection-relevant information is any information that is related to an infection in such a way that a model can use the information to estimate genetic relatedness of two or more infections. In other words, there should be a correlation between a category or type of infection-relevant information and the infection, such that the model can utilize that correlation. Referring to FIG. 3, as just one example, are some possible categories of infection-relevant information 300, although it is not an exhaustive list of types or categories.

According to an embodiment, the infection-relevant information can comprise an antibiotic resistance profile for the patient's infection. Similar pathogens with exhibit similar antibiotic resistance profiles, such that two infections having similar antibiotic resistance profiles can suggest that the two infections are related. The more similar the antibiotic resistance profiles the more suggestion that the two infections are related, and the less similar the antibiotic resistance profiles the more suggestion that the two infections are non-related. This can be a quantifiable correlation utilized by the model. According to just one embodiment, the system may utilize determined Minimum Inhibitory Concentration (MIC) values for up to 37 antibiotics, although many other evaluations are possible.

As another example, the infection-relevant information can comprise a geo-temporal record for the patient. The more time that two people spend in a location, and/or the closer the proximity of the two people to each other, the more suggestion that the two infections are related, and the less time that two people spend in a location, and/or the further the proximity of the two people to each other, the more suggestion that the two infections are non-related. Accordingly, the infection-relevant information can include information about where a person has been located, how long a person has been at one or more locations, and thus can include information about the proximity or distance of two or more people. In the case of surfaces or objects, the infection-relevant information can include information about the location of the surface or object, and what has been in proximity with that surface or object.

As yet another example, the infection-relevant information can comprise a caregiver history for the patient. The more one or more caregivers interact with both of the two infected people, the more suggestion that the two infections are related, and the less that one or more caregivers interact with both of the two infected people, the more suggestion that the two infections are non-related. Accordingly, the infection-relevant information can include information about who has treated, accessed, or otherwise been within a proximity of a patient, surface, or object.

The system also receives pathogen sequencing data for the respective infection associated with each patient used in the analysis. The sequencing data can be obtained from the same database as the infection-relevant information, or can be obtained from a separate database. For example, there may be a separate database comprising sequencing data for each of the pathogens.

At step 120 of the method, the sequencing data is used to calculate genetic relatedness between the infections of two or more of the plurality of patients. The genetic relatedness can be calculated using any known method for evaluating or otherwise calculating genetic distance between two or more sequences. For example, two or more genomic sequences can be compared to identify any differences between the two sequences, where some or all of the differences are utilized for a distance determination. Sample-to-sample genetic distances can calculated and the genetic distance can be reported using any method for reporting genetic distance, including but not limited to a report of the number of single nucleotide polymorphisms (SNPs) differences between each of two or more sequences. For example the comparison of two genetic sequences, which may be partial or whole genome sequences, obtained from two different patients that are known to have a related healthcare-associated infections (HAI) may identify a total of seven (7) SNP differences. Similarly, the comparison of two genetic sequences obtained from two different patients that are known to have non-related infections may identify a total of ten (10) SNP differences for the same type of pathogen. Thus, there may be a meaningful difference between seven and ten SNP differences for genetic relatedness and related versus non-related HAIs.

At step 130 of the method, the system generates a predictive model designed to provide an estimate of genetic relatedness between two or more infections using only infection-relevant information. The system generates the model using the received input, namely the received infection-relevant information and the calculated actual genetic relatedness between two infections, and correlations and/or non-correlations thereof. Using ground truth such as calculated actual genetic relatedness and non-relatedness between infections correlated with one or more aspects of the infection-relevant information associated with those related and non-related infections, a model is generated via machine learning which is able to generate predictions without utilizing sequencing data.

According to an embodiment, the input information is engineered into individual features as a sparse matrix, as shown in FIG. 4. In this embodiment, tach row is a data entry that is a patient pair with the same microbial infection. Each patient pair is a unique entry sorted by the numerical value of patient IDs. For each data entry, the MIC distance is calculated as the ratio of resistance concentration for each antibiotic (Anti-1, Anti-2, Anti-3, etc.) tested. For example, Ampicillin prevents the visible growth of patient 1's sample at >8 (mg/L) while it prevents the growth of patient 2's sample at >32 mg/L. Thus the MIC distance for Ampicillin between the patient pair is 4:

$$MIC\ distance_{Ampicillin}^{pair\ 1,2} = \frac{MIC_{patient\ 2}}{MIC_{patient\ 1}} \qquad \text{Eq. 1}$$

According to an embodiment, missing data is represented in the matrix 0. Other data in the matrix may include, for example, device sharing or other factors that may correlate to infection sharing. Notably, the matrix or similar model-generating analysis can comprise factors not shown in FIG. 4.

Figure 5:
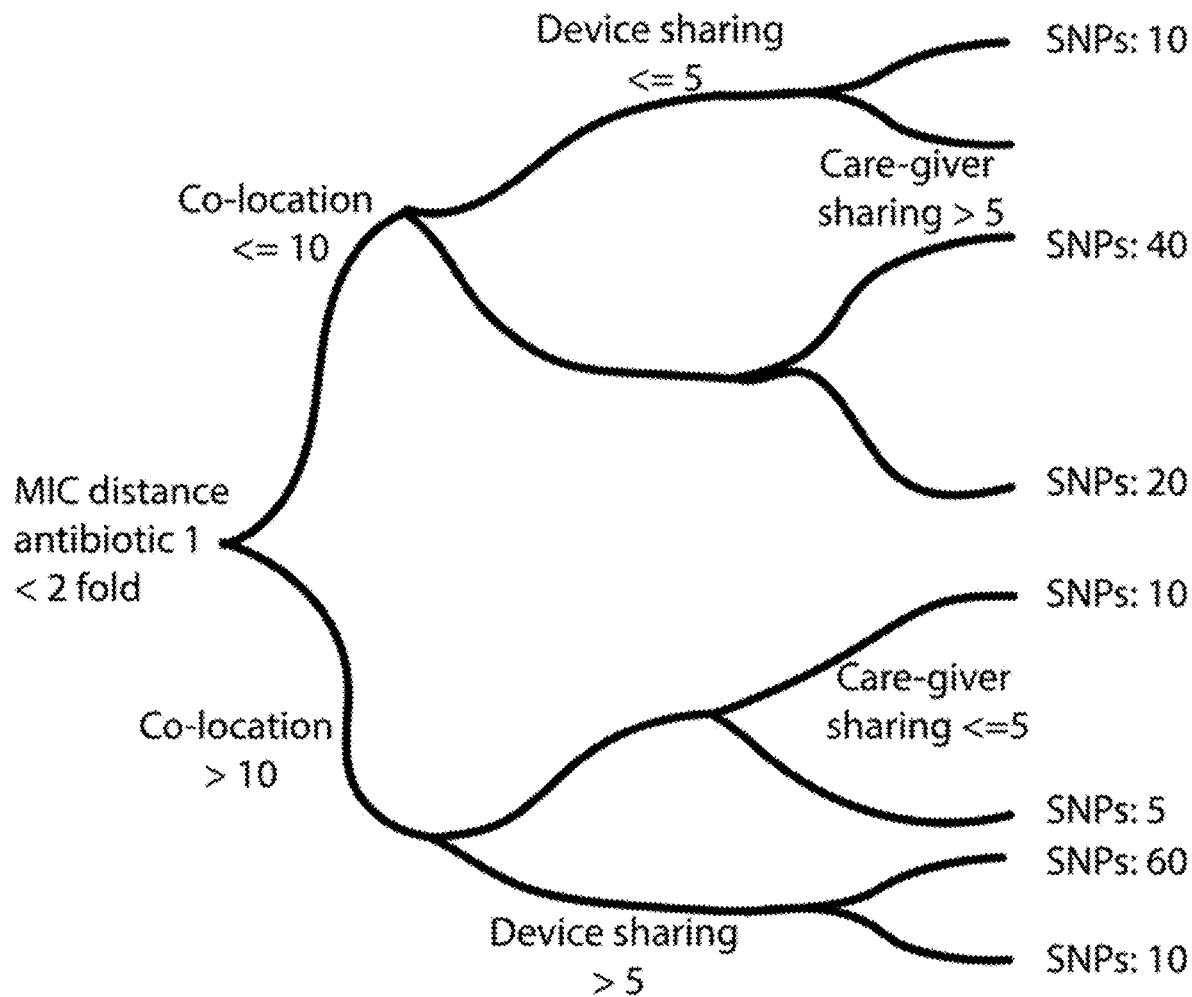
FIG. 5 is a random forest algorithm configured to provide an output as a number of SNPs representing estimated genetic relatedness, in accordance with an embodiment.

According to an embodiment, and as shown in FIG. 5, the normalized input matrix is implemented and optimized on a random forest algorithm to provide an output as the number of SNPs estimated with a confidence interval. The random forest method represents an ensemble of decision trees and an interpretation tree can be generated to help users understand the model. However, many other methods are utilized to generate a predictive model using the normalized input matrix or other input as described or otherwise envisioned herein.

According to an embodiment, a number of SNPs threshold is set to define related infections and non-related infections based at least in part on the species of microbial infection between patients and the known relatedness or non-relatedness of the pathogens. For example, *S. aureus*-related infections may be set at "less than 8 SNPs" while *E. faecium*-related infections may be set at "less than 40 SNPs". These can be user-generated and/or user-defined, and may be modified within the system as necessary. For example, according to an embodiment, a user display may comprise options for adjusting thresholds.

The trained genetic relatedness model may be stored locally or remotely. Accordingly, a system using the genetic relatedness model may access the local or remote storage or processor for the model. The trained genetic relatedness model may be updated or otherwise modified with new or otherwise relevant information, such as new datasets of sequencing information and correlating infection-relevant information, new species of pathogens, and more. For example, a trained genetic relatedness model may be generated, re-trained, or modified for every location at which the model may be implemented. At a minimum, for example, the model can be adjusted to account for differences in locations, proximities, healthcare providers, and other parameters.

Referring to FIG. 2, in one embodiment, is a flowchart of a method 200 for characterizing two or more infections as related or non-related. According to an embodiment, the two or more infections are identified at, and possibly obtained from for subsequent analysis, any source. For example, an infection pathogen may be obtained from a person, a surface, an air sample, and/or any other location. Accordingly, the method may compare the infections or pathogen of two or more people, surfaces, locations, or comparing the infections or pathogen of people versus objects or surfaces, among other possibilities. The infection may be identified for analysis using any method of identification, including visual identification, identification via one or more symptoms, and many other methods.

At step 210 of the method, the system receives infection-relevant information for each of two or more infected patients. Method 200 may be initiated in response to a healthcare professional identifying a pathogen or infection that might be a related HAI, and/or may be initiated as part of an automated protocol. As an example, the system may perform this analysis for any patient identified with any infection, or for any patient identified with a specific infection. Many other parameters for initiation of the method are possible.

As described in detail above, infection-relevant information is any information that is related to an infection in such a way that a model can use the information to estimate genetic relatedness of two or more infections. In other words, there should be a correlation between a category or type of infection-relevant information and the infection, such that the model can utilize that correlation. According to an embodiment, the infection-relevant information can comprise antibiotic resistance profiles for the patients' infections, geo-temporal records for the patients, caregiver histories for the patients, and/or other information about the patients or their care. Other infection-relevant information is also possible.

The system may receive infection-relevant information via a user interface input, and/or may receive the information from a local or remote source such as an electronic medical record. For example, a healthcare professional may identify two people as potentially comprising a related HAI, and may direct the system to automatically contact stored electronic records for the two people in order to perform the analysis.

At step 220 of the method, the system estimates the genetic relatedness of the infections/pathogens of the two patients, using the trained genetic relatedness model analyzing the received infection-relevant information. As described in detail herein, the system has been trained with both infection-relevant information and sequencing data to develop a genetic relatedness model that can create an estimate of infection relatedness using infection-relevant information without sequencing data. The trained genetic relatedness model may be stored locally or remotely. Accordingly, the system may access the local or remote storage or processor for the model.

The trained genetic relatedness model generates a genetic relatedness estimate output which is used in downstream steps of the method. According to an embodiment, the output of the model is at least a predicted number of SNPs between the two or more infections, although other outputs are possible. The output may be utilized immediately or may be stored for future use.

At step 230 of the method, the system compares the estimated genetic relatedness output to a predetermined threshold. The threshold may be predetermined by a user, by another algorithm, or by any other means, and may be modified within the system as necessary. For example, according to an embodiment, a user display may comprise options for adjusting thresholds. According to an embodiment, the threshold may be a number of SNPs threshold which defines infections as being related or non-related. Thus, the threshold may be at least in part based on the species or other identifying information of the pathogens or infections.

At step 240 of the method, the system identifies the infections as being related infections or non-related infections based on the comparison with the one or more thresholds. For example, the infections may be identified as a related infection if the estimated genetic relatedness falls below the predetermined threshold, and the infections may be identified as a non-related infection if the estimated genetic relatedness exceeds the predetermined threshold.

For example, S. aureus infections may comprise a threshold of 8 SNPs, meaning that an estimated genetic relatedness output of 6 SNPs for an S. aureus infection indicates that the infections are related and an estimated genetic relatedness output of 9 SNPs for an S. aureus infection indicates that the infections are non-related.

At step 250 of the method, a report of the estimated genetic relatedness output is provided to a user via a user display or other communication system or device. Additionally and/or alternatively, the report comprises information about two or more infections being related or non-related based on the analysis. For example, the report may comprise information about the patients such as their identity, the infection-relevant information associated with the patients, information about their infections, the estimated genetic relatedness output for the infections, and/or an indication that the infections are related or non-related based on the threshold comparison. According to an embodiment, the representation of the estimated genetic relatedness can include a network graph of the patients and/or infections.

According to an embodiment, the user display may be an interactive user display. For example, the user display may display a network graph of genetically related patients set by the above threshold, and the user can select patients of interest to see detailed information of patients' stay in a table format or any other format. The user may also be able to adjust thresholds or other parameters of the system or genetic relatedness model. Other implementations of an interactive user display are possible.

According to an embodiment, further analysis of an infection may be necessary, suggested, desired, or triggered if infections are identified by the method and model as being related. For example, an indication that two infections are related may indicate an HAI problem, and thus may necessitate further investigation. However, since the model will only identify some infections as being related, the method and system reduce costs and save resources by obviating the need to sequence infections that are non-related based on the analysis.

Thus, at step 260 of the method sequencing data for each of the infections/pathogens is obtained by the system if infections are identified by the method and model as being related. The sequencing data may be obtained by the system or may otherwise be accessed by or provided to the system. According to an embodiment, the system may comprise a sequencer that generates the sequencing data. Alternatively, the system may be in communication with a database or memory or storage comprising the sequencing data. The sequencing data may be partial or whole genome sequences.

At step 270 of the method, the system determines the actual genetic relatedness of the infections using the obtained sequencing data. The genetic relatedness can be calculated using any known method for evaluating or otherwise calculating genetic distance between two or more sequences. For example, the sequences can be compared to identify any differences between the two sequences, where some or all of the differences are utilized for a distance determination. Sample-to-sample genetic distances can calculated and the genetic distance can be reported using any method for reporting genetic distance, including but not limited to a report of the number of single nucleotide polymorphisms (SNPs) differences between each of two or more sequences. According to an embodiment, the determined the actual genetic relatedness of the infections can be reported to the user via the user display or other communication system or device.

Figure 6:
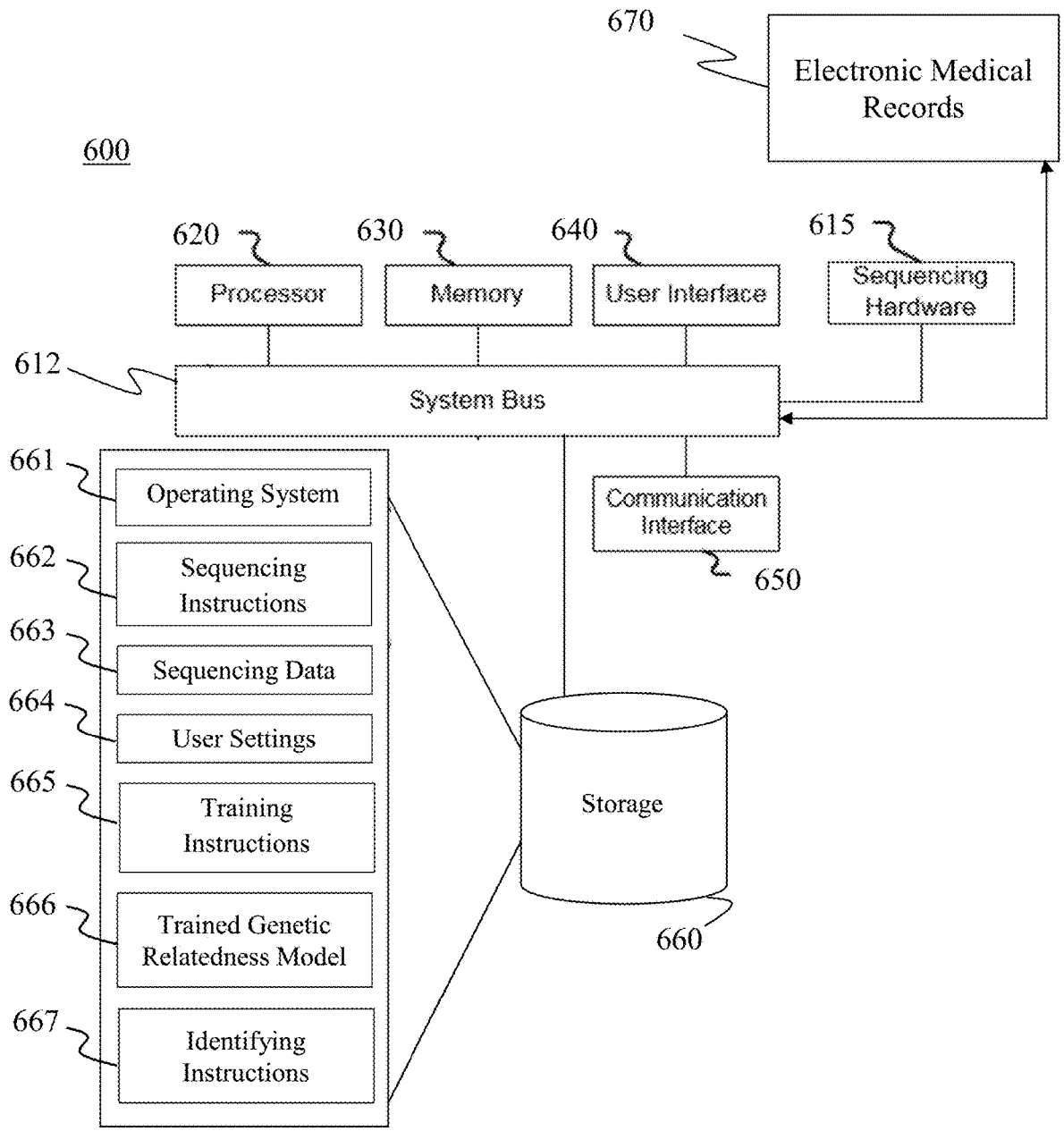
FIG. 6 is a schematic representation of a system configured to characterize two or more infections as related or non-related, in accordance with an embodiment.

Referring to FIG. 6, in one embodiment, is a schematic representation of a system 600 for identifying two or more infections as related or non-related infections based on an estimated genetic relatedness of the two or more infections. System 600 may be any of the systems described or otherwise envisioned herein, and may comprise any of the components described or otherwise envisioned herein.

According to an embodiment, system 600 comprises one or more of a processor 620, memory 630, user interface 640, communications interface 650, and storage 660, interconnected via one or more system buses 612. In some embodiments, such as those where the system comprises or directly implements a sequencer or sequencing platform, the hardware may include additional sequencing hardware 615 such as a real-time single-molecule sequencer, including but not limited to a pore-based sequencer, although many other sequencing platforms are possible. It will be understood that FIG. 6 constitutes, in some respects, an abstraction and that the actual organization of the components of the system 600 may be different and more complex than illustrated.

According to an embodiment, system 600 comprises a processor 620 capable of executing instructions stored in memory 630 or storage 660 or otherwise processing data to, for example, perform one or more steps of the method. Processor 620 may be formed of one or multiple modules. Processor 620 may take any suitable form, including but not limited to a microprocessor, microcontroller, multiple microcontrollers, circuitry, field programmable gate array (FPGA), application-specific integrated circuit (ASIC), a single processor, or plural processors.

Memory 630 can take any suitable form, including a non-volatile memory and/or RAM. The memory 630 may include various memories such as, for example L1, L2, or L3 cache or system memory. As such, the memory 630 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 600. It will be apparent that, in embodiments where the processor implements one or more of the functions described herein in hardware, the software described as corresponding to such functionality in other embodiments may be omitted.

User interface 640 may include one or more devices for enabling communication with a user. The user interface can be any device or system that allows information to be conveyed and/or received, and may include a display, a mouse, and/or a keyboard for receiving user commands. In some embodiments, user interface 640 may include a command line interface or graphical user interface that may be presented to a remote terminal via communication interface 650. The user interface may be located with one or more other components of the system, or may located remote from the system and in communication via a wired and/or wireless communications network.

Communication interface 650 may include one or more devices for enabling communication with other hardware devices. For example, communication interface 650 may include a network interface card (NIC) configured to communicate according to the Ethernet protocol. Additionally, communication interface 650 may implement a TCP/IP stack for communication according to the TCP/IP protocols. Various alternative or additional hardware or configurations for communication interface 650 will be apparent.

Storage 660 may include one or more machine-readable storage media such as read-only memory (ROM), random-access memory (RAM), magnetic disk storage media, optical storage media, flash-memory devices, or similar storage media. In various embodiments, storage 660 may store instructions for execution by processor 620 or data upon which processor 620 may operate. For example, storage 660 may store an operating system 661 for controlling various operations of system 600. Where system 600 implements a sequencer and includes sequencing hardware 615, storage 660 may include sequencing instructions 662 for operating the sequencing hardware 615, and sequencing data 663 obtained by the sequencing hardware 615. Storage 660 may also store user settings 664 such as predetermined thresholds, and other elements.

It will be apparent that various information described as stored in storage 660 may be additionally or alternatively stored in memory 630. In this respect, memory 630 may also be considered to constitute a storage device and storage 660 may be considered a memory. Various other arrangements will be apparent. Further, memory 630 and storage 660 may both be considered to be non-transitory machine-readable media. As used herein, the term non-transitory will be understood to exclude transitory signals but to include all forms of storage, including both volatile and non-volatile memories.

While system 600 is shown as including one of each described component, the various components may be duplicated in various embodiments. For example, processor 620 may include multiple microprocessors that are configured to independently execute the methods described herein or are configured to perform steps or subroutines of the methods described herein such that the multiple processors cooperate to achieve the functionality described herein. Further, where one or more components of system 600 is implemented in a cloud computing system, the various hardware components may belong to separate physical systems. For example, processor 620 may include a first processor in a first server and a second processor in a second server. Many other variations and configurations are possible.

According to an embodiment, storage 660 of system 600 may store one or more algorithms and/or instructions to carry out one or more functions or steps of the methods described or otherwise envisioned herein. For example, processor 620 may comprise one or more of training instructions 665, a trained genetic relatedness model 666, and identifying instructions 667.

According to an embodiment, training instructions 665 direct the system to generate, using input data described or otherwise envisioned herein, a genetic relatedness model configured to perform the subsequent estimation of genetic relatedness of two or more infections. As an example, the input may comprise infection-relevant information and pathogen sequencing data for a plurality of patients and their respective infection. The training instructions 665 direct the system to process the input data to train a model that can utilize input data—without sequencing data—to estimate genetic relatedness of two or more infections. According to an embodiment, the training instructions 665 direct the system to create the model using the method described or otherwise envisioned herein.

According to an embodiment, the trained genetic relatedness model 666 is utilized by the system to estimate genetic relatedness of two or more infections without sequencing data. The trained genetic relatedness model 666 can be created by the system as described or otherwise envisioned herein, and may optionally be stored or otherwise made available for processing input data such as the infection-relevant information described herein. The output of the trained genetic relatedness model 666 is a genetic relatedness estimate which is used in downstream steps of the method. According to an embodiment, the output of the model is at least a predicted number of SNPs between the two or more infections, although other outputs are possible.

According to an embodiment, identifying instructions 667 direct the system to compare the genetic relatedness estimate output from the trained genetic relatedness model 666 to one or more predetermined thresholds in order to make a relatedness determination. For example, the identifying instructions 667 may direct the system to identify two or more infections as related infection if the estimated genetic relatedness output falls below the predetermined threshold, and/or to direct the system to identify the two or more infections as non-related infection if the estimated genetic relatedness output exceeds the predetermined threshold. This determination can be stored in local or remote storage and/or communicated locally or remotely, such as via user interface 640.

The system may also comprise or be in communication with a database 670 of electronic medical records. For example, the system may request or receive infection-relevant information from a local or remote source such as an electronic medical record database 670. For example, a healthcare professional may identify two people as potentially comprising a related HAI, and may direct the system to automatically contact stored electronic records for the two people in order to perform the analysis.

The genetic relatedness system and method described or otherwise envisioned herein provides numerous advantages over existing systems. For example, the system improves the efficiency and speed with which infections can be analyzed. Instead of requiring genomic sequencing, which is time-expensive, the system can utilize existing data. This frees sequencing hardware for other operations. In a clinical setting where genomic analysis is become increasingly important, minimizing sequencing time while ensuring sequencing sufficiency is extremely beneficial and valuable. More samples can be analyzed in a shorter amount of time, thereby enabling faster diagnosis and treatment, which can significantly improve treatment outcomes.

In a clinical setting, quickly and affordably identifying related HAIs allow for the treatment and prevent of infection. Identifying and quarantining/treating infection is an enormous benefit of the present invention, and meets several different continued needs in the art. Using the approach and/or system described or otherwise envisioned herein, a clinician or other healthcare provider can make significantly improved and more informed decisions, and can better treat dangerous and often life-threatening infections.

The system also saves considerable expense. Existing systems used to analyze possible HAIs require sequencing data for each of the two or more infections, which is costly. The present system, however, obviates the need for sequencing data unless the infections are identified by the model as being related. Since only a small percentage of screened infections are expected to be dangerous related HAIs, the system prevents the unnecessary sequencing of thousands of samples, saving enormous expense, time, and other resources.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for identifying two or more infections as related or non-related infections based on an estimated genetic relatedness of the two or more infections, comprising:
    training a genetic relatedness model, comprising: (i) receiving, from a database of infection data, infection-relevant information for a plurality of patients and pathogen sequencing data for an infection associated with each of the plurality of patients; (ii) calculating, using the sequencing data, genetic relatedness between the infections of two or more of the plurality of patients; and (iii) generating, from the received infection-relevant information and the calculated genetic relatedness between the infections, a predictive model designed to provide an estimate of genetic relatedness between two or more infections using only infection-relevant information;
    receiving, for each of two or more infected patients, infection-relevant information comprising an antibiotic resistance profile for the patient's infection, a geo-temporal record for the patient, and a caregiver history for the patient;
    estimating, using the trained genetic relatedness model analyzing the received infection-relevant information for the two or more infected patients, a genetic relatedness of at least two of the two or more infections;
    comparing the estimated genetic relatedness between at least two of the two or more infections to a predetermined threshold; and
    identifying, based on the comparison, the at least two of the two or more infections as a related infection or a non-related infection, wherein the at least two of the two or more infections are identified as a related infection if the estimated genetic relatedness falls below the predetermined threshold, and wherein the at least two of the two or more infections are identified as a non-related infection if the estimated genetic relatedness exceeds the predetermined threshold.

2. The method of claim 1, wherein, once trained, the trained genetic relatedness model estimates genetic relatedness of the at least two of the two or more infections without sequencing data.

3. The method of claim 1, wherein the genetic relatedness of the two or more infections comprises a predicted number of SNPs between at least two of the two or more infections.

4. The method of claim 1, further comprising:
    obtaining, if the at least two of the two or more infections are identified as related, sequencing data for each of the at least two of the two or more infections; and
    determining, using the obtained sequencing data, the relatedness of the at least two of the two or more infections.

5. The method of claim 1, further comprising:
    displaying, on an interactive user interface, a representation of the estimated genetic relatedness between the at least two of the two or more infections.

6. The method of claim 5, wherein the representation of the estimated genetic relatedness comprises a network graph of two or more patients and/or infections.

7. The method of claim 1, further comprising:
    adjusting, using an interactive user interface, the predetermined threshold.

8. The method of claim 1, wherein the predetermined threshold is based at least in part on the identity of a pathogen causing the two or more infections.

9. The method of claim 1, wherein the genetic relatedness model comprises a decision tree.

10. A system configured to identify two or more infections as related or non-related infections based on an estimated genetic relatedness of the two or more infections, comprising:
    infection-relevant information for each of two or more infected patients, comprising an antibiotic resistance profile for the patient's infection, a geo-temporal record for the patient, and a caregiver history for the patient;
    a trained genetic relatedness model configured to analyze the received infection-relevant information for the two or more infected patients and to estimate based on that analysis a genetic relatedness of at least two of the two or more infections, wherein the genetic relatedness model is trained by: (i) receiving, from a database of infection data, infection-relevant information for a plurality of patients and pathogen sequencing data for an infection associated with each of the plurality of patients; (ii) calculating, using the sequencing data, genetic relatedness between the infections of two or more of the plurality of patients; and (iii) generating, from the received infection-relevant information and the calculated genetic relatedness between the infections, a predictive model designed to provide an estimate of genetic relatedness between two or more infections using only infection-relevant information;

a processor configured to:
  (i) compare the estimated genetic relatedness between at least two of the two or more infections to a predetermined threshold; and
    (i) identify, based on the comparison, the at least two of the two or more infections as a related infection or a non-related infection, wherein the at least two of the two or more infections are identified as a related infection if the estimated genetic relatedness falls below the predetermined threshold, and wherein the at least two of the two or more infections are identified as a non-related infection if the estimated genetic relatedness exceeds the predetermined threshold; and a user interface configured to display a representation of the estimated genetic relatedness between the at least two of the two or more infections.

11. The system of claim 10, wherein the representation of the estimated genetic relatedness comprises a network graph of two or more patients and/or infections.

12. The system of claim 10, wherein, once trained, the trained genetic relatedness model estimates genetic relatedness of the at least two of the two or more infections without sequencing data.

13. The system of claim 10, wherein the predetermined threshold is based at least in part on the identity of a pathogen causing the two or more infections.

14. The system of claim 10, wherein the genetic relatedness of the two or more infections comprises a predicted number of SNPs between at least two of the two or more infections.

* * * * *